United States Patent [19]

Deters et al.

[11] Patent Number: 4,627,850
[45] Date of Patent: Dec. 9, 1986

[54] OSMOTIC CAPSULE

[75] Inventors: Joseph C. Deters, Mountain View; Felix Theeuwes, Los Altos; Kevin J. Mullins, Berkeley; James B. Eckenhoff, Los Altos, all of Calif.

[73] Assignee: ALZA Corporation, Palo Alto, Calif.

[21] Appl. No.: 548,219

[22] Filed: Nov. 2, 1983

[51] Int. Cl.$^4$ .................................. A61M 31/00
[52] U.S. Cl. .................................. 604/892; 604/890; 424/21; 424/19; 428/308.4; 428/318.6; 428/478.4; 106/169; 106/196; 526/930; 210/500.28; 210/500.29; 210/500.30; 210/500.31; 210/500.32; 210/500.35; 210/500.38; 210/500.42
[58] Field of Search ............... 428/308.4, 318.6, 321.5, 428/478.4, 479.3; 210/500.2, 506; 604/892, 893, 896; 106/122, 196; 424/21, 19; 526/930

[56] References Cited

U.S. PATENT DOCUMENTS

| | | | |
|---|---|---|---|
| 4,077,407 | 3/1978 | Theeuwes et al. | 106/196 X |
| 4,116,241 | 9/1978 | Theeuwes et al. | 604/893 |
| 4,256,108 | 3/1981 | Theeuwes | 604/893 |
| 4,327,725 | 5/1982 | Cortese et al. | 604/893 |
| 4,331,728 | 5/1982 | Theeuwes | 210/500.2 X |
| 4,455,144 | 6/1984 | Michaels | 604/892 |
| 4,500,358 | 2/1985 | Mayer et al. | 106/122 |

Primary Examiner—Joseph L. Schofer
Assistant Examiner—F. M. Teskin
Attorney, Agent, or Firm—Paul L. Sabatine; Edward L. Mandell; Steven F. Stone

[57] ABSTRACT

An osmotic capsule is disclosed for delivering a beneficial agent formulation to an environment of use. The osmotic capsule comprises an outer semipermeable wall surrounding and laminating an inner capsule wall formed of a different polymeric composition than the outer wall. The walls define an interior space containing the beneficial agent formulation. A passageway through the walls connects the exterior of the osmotic capsule with the interior of the osmotic capsule.

26 Claims, 8 Drawing Figures

OSMOTIC CAPSULE

FIELD OF THE INVENTION

This invention relates to an osmotic capsule. More particularly, the invention pertains to an osmotic capsule comprising a wall capsuling a compartment containing a useful agent. The wall comprises (1) a first lamina capsuling and facing the compartment and formed of a material that swells at a controlled rate in the presence of fluid and, (2) a second lamina capsuling the first lamina and formed in at least a part of a material permeable to the passage of fluid and substantially impermeable to the passage of useful agent. The osmotic capsule comprises an orifice through the wall that connects the exterior of the osmotic capsule with the interior compartment for delivering the useful agent from the osmotic capsule over time.

BACKGROUND OF THE INVENTION

Capsules are a dosage form in whcih a useful agent is enclosed within a wall. Capsules are a popular method for administering a useful agent in both prescription practice and in over-the-counter practice, and they are widely used in hospitals, in homes, and in other environments. Capsules enjoy this popularity because they are tasteless, essentially innocuous, easily administered, and they are easily filled extemporaneously or in large numbers. Additionally, some users find it easier to swallow capsules than other dosage forms.

While these advantages and preferences have lead to the continuing acceptance of capsules, there are certain short comings associated with capsules. For example, capsules give up all their useful agent immediately to the environment of use, with the consequence that useful agent concentration is high initially followed by a low concentration, or by a total absence of useful agent between later administered capsules. For many useful agents this form of administration can have undesirable effects, especially if the useful agent has a low therapeutic index and is not suited to time-varying rates of administration. Another shortcoming associated with capsules is they are poorly suited for administering useful agents with short biological half-lives, and this results in exclusion of a large number of useful agents including mammalian biochemicals, natural hormones, humoral factors, and the like.

Yet another shortcoming associated with capsules is their instant delivery of a useful agent and its accompanying detrimental effects. Because of this, capsules require a high frequency of use, and this often leads to a failure of patient compliance for a prescribed dosage schedule. Such failures are reflected in a lack of therapeutic effectiveness and in possible toxic effects. The latter effects can occur when patients double or triple their dosage to compensate for their prior omissions. Faulty compliance accompanying the use of capsules is a common and largely ignored problem.

It will be appreciated by those versed in the art in the light of this presentation, that if an osmotic capsules can be provided that is free of the tribulations known to the prior art, such an osmotic capsule would have a positive, practical value and it would also represent an advancement in the delivery art. The present invention advances the state of the delivery art by providing a delivery system manufactured as an osmotic capsule for optimizing the beneficial effects of a useful agent. The osmotic capsule administers the useful agent at a programmed and controlled rate for a prescribed period of time. The osmotic capsule provides continuous control over the administration of the useful agent, and it maintains this control over an extended period of time.

OBJECTS OF THE INVENTION

Accordingly, it is an immediate object of this invention to provide a delivery system manufactured as an osmotic capsule for the delivery of a useful agent at a controlled rate over a prolonged period of time, with the osmotic capsule representing both an improvement and an advancement in the delivery arts.

Yet another object of the invention is to provide an osmotic capsule that can house a useful agent formulation comprising solutions, oils, emulsions, sols, and suspensions, and can deliver the useful agent at a controlled rate and continuously over a prolonged period of time.

Yet still another object of the invention is to provide an osmotic capsule that contains a useful agent formulation in solid, powdered, pulverized, micronized, and particle forms, which forms in the presence of fluid imbibed into the osmotic capsule form a solution or suspension that is delivered from the osmotic capsule, and which osmotic capsule maintains its physical and chemical integrity, is simple in construction, and exhibits all the practical benefits of controlled and continuous administration of the useful agent formulation during the osmotic capsule's residency in the environment of use over a prolonged period of time.

Still another object of the invention is to provide an osmotic capsule for administering a drug in the gastrointestional tract by making available an osmotic capsule comprising at least one wall that maintains its integrity in the gastrointestional tract during its complete transit therethrough.

Yet still another object of the invention is to provide an osmotic capsule comprising a wall capsulating a drug formulation that optionally includes a pharmaceutically acceptable carrier, and which drug can be delivered by the osmotic capsule at meaningful and useful rates over a prolonged period of time.

Yet still another object of the invention is to provide an osmotic capsule comprising a wall comprising an interior lamina formed of a water-swellable material that swells at a controlled rate and encapsulates a drug formulation, and an exterior lamina formed of a semipermeable material that maintains its integrity and encapsulates the interior lamina.

Still yet another object of the invention is to provide an osmotic capsule comprising a compartment containing a useful agent formulation and a pharmaceutically acceptable carrier, which compartment is capsuled by a wall having an osmotic orifice for delivering the useful agent from the capsule over a prolonged period of time of at least 15 minutes.

Other objects, features, aspects and advantages of the invention will be more apparent to those versed in the art from the following detailed specification taken in conjunction with the drawings and the accompanying claims.

BRIEF DESCRIPTION OF THE DRAWINGS

In the drawing figures, which are not drawn to scale, but are set forth to illustrate various embodiments of the invention, the drawing figures are as follows.

In the drawings and the specification, like parts in related figures are identified by like parts. The terms appearing earlier in the specification and in the description of the drawings, as well as embodiments thereof, are further detailed elsewhere in the disclosure.

DETAILED DESCRIPTION OF THE DRAWINGS

Figure 1:
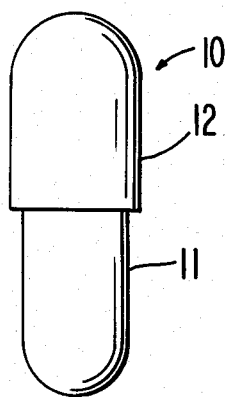
FIG. 1 is a view of an osmotic capsule made of two parts, comprising a body portion telescopically capped by an engaging cap portion.

Turning now to the drawings figures in detail, which figures are examples of osmotic capsules provided by the invention, and which examples are not to be construed as limiting, one example of an osmotic capsule is seen in FIG. 1. In FIG. 1, osmotic capsule 10 is seen comprising two parts, a body member 11, and a cap member 12. The osmotic capsule 10 of FIG. 1 is made conveniently in two parts with one part 12 slipping over and capping the other part 11. Osmotic capsule parts 11 and 12 completely surround and capsulate an internal lumen containing an active agent, not seen in FIG. 1.

Figure 2:
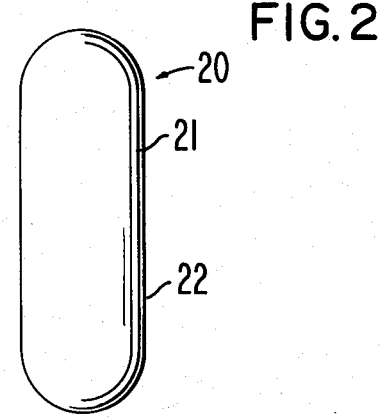
FIG. 2 is a view of an osmotic capsule made as a one piece, sealed osmotic capsule for enclosing a useful agent.

FIG. 2 depicts osmotic capsule 20 comprising a body 21 formed of a wall 22 capsuling an internal space, not seen in FIG. 2. Osmotic capsule 20 of FIG. 2 is made in its final manufacture as a single unit osmotic capsule. That is, osmotic capsule 20 cannot be easily separated into original parts. Osmotic capsule 20 contains in its internal space a useful agent, not seen in FIG. 2.

Osmotic capsule 10 of FIG. 1, and osmotic capsule 20 of FIG. 2, possess two distinct forms, classified for the purpose of this invention, as osmotic hard capsule 10 as seen in FIG. 1, and osmotic soft capsule 20 as seen in FIG. 2. The osmotic hard capsule is composed of two parts, a cap and a body, which are fitted together after the larger body is filled with a preselected appropriate agent formulation. This is done by slipping or telescoping the cap section over the body section, thus completely surrounding and encapsulating the useful agent formulation. Hard capsules are made by dipping stainless steel molds into a bath containing a solution of a capsule lamina-forming material to coat the mold with the material. Then, the molds are withdrawn, cooled, and dried in a current of air. The capsule is stripped from the mold and trimmed to yield a lamina member with an internal lumen. The engaging cap that telescopically caps the agent formulation receiving body is made in a similar manner. Then, the closed and filled osmotic capsule is capsuled with a semipermeable lamina. The semipermeable lamina can be applied to capsule parts 11 and 12 of FIG. 1 either before or after parts 11 and 12 are joined into the final capsule 10. In another embodiment, the hard capsules can be made with each part having, matched locking rings near their opened end that permit joining and locking together the overlapping cap and body after filling with agent formuation. In this embodiment, a pair of matched locking rings are formed into the cap portion and the body portion, and these rings provide the locking means for securely holding together the capsule. The capsule can be manually filled with the agent formulation, or they can be machine filled with the agent formulation. In the final manufacture the hard capsule is capsuled with a semipermeable lamina permeable to the passage of fluid and substantially impermeable to the passage of useful agent as described hereafter.

The osmotic soft capsule as used by the present invention, preferably in its final form, comprises one piece. Generally, the osmotic soft capsule is of sealed construction encapsulating the useful agent formulation therein. The soft capsule is made by various processes including the plate process, the rotary die process, the reciprocating die process, and the continuous process. The place process uses a set of molds. A warm sheet of a prepared capsule lamina-forming material is laid over the lower mold and the agent formulation poured on it. A second sheet of the lamina-forming material is placed over the agent formulation followed by the top mold. The mold set is placed under a press and a pressure applied, with or without heat to form a unit, soft capsule. The capsules are washed with a solvent for removing excess agent formulation from the exterior of the capsule, and the air-dried capsule is capsuled with a lamina of a semiper-meable material.

The rotary die process uses two continuous films of capsule lamina-forming material that are brought into convergence between a pair of revolving dies and an injector wedge. The process fills and seals the capsule in dual and coincident operations. In this process, the sheets of capsule lamina-forming material are fed over guide rolls, and then down between the wedge injector and the die rolls. The agent formulation to be capsuled flows by gravity into a positive displacement pump. The pump meters the agent formulation through the wedge injector and into the sheets between the die rolls. The bottom of the wedge contains small orifices lined up with the die pockets of the die rolls. The capsule is about half-sealed when the pressure of pumped agent formulation forces the sheets into the die pockets, wherein the soft capsules are simultaneously filled, shaped, hermetically sealed and cut from the sheets of lamina-forming materials. The sealing of the soft capsule is achieved by mechanical pressure on the die rolls and by heating of the sheets of lamina-forming materials by the wedge. After manufacture, the agent formulation-filled capsules are dried in the presence of forced air, and a semipermeable lamina capsuled thereto, by processes described hereafter.

The reciprocating die process produces soft capsules by leading two films of capsule lamina-forming material between a set of vertical dies. The dies as they close, open, and close perform as a continuous vertical plate forming row after row of pockets across the film. The pockets are filled with agent formulation, and as the pockets move through the dies, they are sealed, shaped and cut from the moving film as capsules filled with agent formulation. A semipermeable capsulating lamina is coated thereon to yield the osmotic, soft capsule. The continuous process is a manufacturing system that also uses rotary dies with the added feature that the process can successfully fill active agent in dry powder form into a soft capsule, in addition to encapsulating liquids. The filled, soft capsule of the continuous process is encapsulated with a semipermeable polymeric material to yield the osmotic soft capsule.

Figure 3:
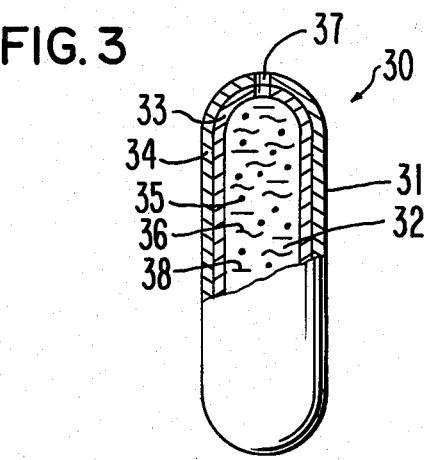
FIG. 3 is an opened view of an osmotic capsule for illustrating the internal structure of the osmotic capsule.

FIG. 3 depicts an osmotic capsule 30 in opened section. Osmotic capsule 30 comprises a wall 31 that capsules or surrounds an inner compartment 32. Wall 31 is permeable in at least a part to the passage of fluid present in the environment of use, and it is substantially impermeable to the passage of active agent, and the like. Wall 31 comprises a first lamina 33 that faces compartment 32, and a second lamina 34 that capsules lamina 33, and faces in FIG. 3 the environment of use. Lamina 33 is formed of a hydrophilic, polymeric composition that swells in the presence of aqueous and biological fluids imbibed into compartment 32. Lamina 33 can exhibit an osmotic pressure gradient across lamina 34 against an exterior fluid. Lamina 33 is non-toxic and it does not adversely affect the contents in compartment 32. Lamina 34 is formed of a semipermeable polymeric composition that is substantially permeable to the passage of an exterior fluid, substantially impermeable to the passage of useful agents and the like, it is non-toxic, and it maintains its physical and chemical integrity during the life of osmotic capsule 30. In another presently preferred embodiment, lamina 34 is formed of a composition comprising a semipermeable material that maintains its physical and chemical integrity independent of pH and at least one other lamina forming material that maintains its physical and chemical integrity in a pH of from 1 to 3.5 and loses its integrity in an environment having a pH greater than 3.5. The osmotic capsule contains an osmotic orifice 37 through wall 31 that connects compartment 32 with the exterior of osmotic capsule 30 for delivering useful agent 35 to a fluid environment of use.

Compartment 32 contains an effective amount of useful agent 35, represented by dots, and in a presently preferred embodiment a pharmaceutically acceptable carrier 36 therefore, represented by wavy lines. Useful agent 35 can exhibit an osmotic pressure gradient across wall 31 against an exterior fluid, or it may possess limited solubility and it may not exhibit any osmotic pressure gradient across wall 31 against the exterior fluid. In this latter embodiment, when useful agent 35 has a limited solubility, or if it is substantially insoluble in fluid imbibed into compartment 32, pharmaceutically acceptable carrier 36 can exhibit an osmotic pressure gradient across wall 31 against an exterior fluid for providing the hydrodynamic driving force for delivering useful agent 35 from osmotic capsule 30. Or, compartment 32 can contain a pharmaceutical carrier that exhibits no osmotic gradient and is hydrophobic in character. Additionally, compartment 32 can contan an osmagent that is soluble in exterior fluid and exhibit an osmotic pressure gradient across wall 31.

Figure 4:
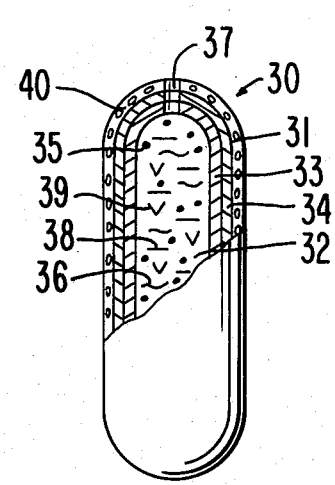
FIG. 4 is an opened view of an osmotic capsule for illustrating another laminated wall of the osmotic capsule.

Wall 31 and compartment 32 operate to substantially insure the delivery of useful agent 35 from compartment 32 at a controlled rate and continuously over a prolonged period of time. In one operation, useful agent 35 is delivered by hydrophilic lamina 33 imbibing and absorbing external fluid across semipermeable lamina 34, causing lamina 33 to swell and expand to some enlarged state. As lamina 33 continuously increases its volume and expands into compartment 32, it urges useful agent 35 through osmotic passageway 37 at a corresponding controlled rate and continuously over a prolonged period of time. In another operation, osmotic capsule 30 releases useful agent 35 by fluid being imbibed into compartment 32 in a tendency towards osmotic equilibrium at a rate determined by the permeability of wall 31 and the osmotic pressure gradient across wall 31. The imbibed fluid 38 continuously forms with agent formulation in the capsule a solution, or a suspension, or an emulsion containing useful agent 35 and the carrier, or the imbibed fluid does not substantially interact with the carrier, or osmagent as seen in FIG. 4, which causes agent 35 to be osmotically delivered through passageway 37 from osmotic capsule 30. Useful agent 35 can be delivered by a combination of these operations, simultaneously with the osmotic activity in compartment 32.

FIG. 4 shows another embodiment of osmotic capsule 30. Osmotic capsule 30 consists essentially of wall 31 which wall 31 comprises lamina 33 a first or inside lamina, lamina 34 a second or middle lamina, and lamina 40 a third or outside lamina. Lamina 40 is a microporous lamina that is preformed or formed in the environment of use, when osmotic capsule 30 is in operation therein. Microporous lamina 40 is laminated to semipermeable lamina 34, which semipermeable lamina 34 is in laminar arrangement with hydrophilic lamina 33. In an embodiment lamina 40 is formed of a pH sensitive material that maintains its integrity in a pH of up to 3.5 and loses its physical and chemical integrity in an environment having a pH greater than 3.5. Compartment 32 is capsuled by the trilaminated wall. Compartment 32 contains useful agent 35, pharmaceutically acceptable carrier 36, optionally osmagent 39, and during operation imbibed fluid 38. Osmotic orifice 37 communicates with compartment 32 and the exterior of osmotic capsule 30. In another embodiment, not shown, a microporous lamina can be in laminar arrangement with the hydrophilic lamina, and a semipermeable lamina can face the environment of use and be in laminar arrangement with the microporous lamina.

Figure 5:
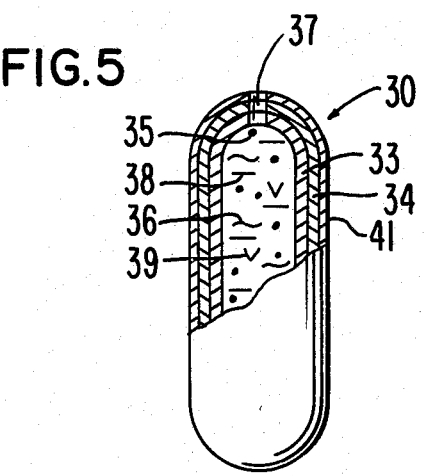
FIG. 5 is an opened view of an osmotic capsule depicting the internal structure of the osmotic capsule and a fluid impermeable lamina on at least a part of the osmotic capsule.

FIG. 5 depicts another embodiment of the invention. In this embodiment, osmotic capsule 30 is coated in part with a lamina 41 formed of a polymeric material substantially impermeable to the passage of fluid. Lamina 41 is coated onto the total capsule, or onto the upper or lower area by dipping the capsule or a part of osmotic capsule 30 into a solution containing a polymer substantially impermeable to fluid. When the osmotic capsule is coated in part with a fluid impermeable polymer, the reaminder of the lamina is formed of a material permeable to fluid. This coating with the impermeable polymer is especially useful for the part of the osmotic capsule containing the orifice.

Figure 6:
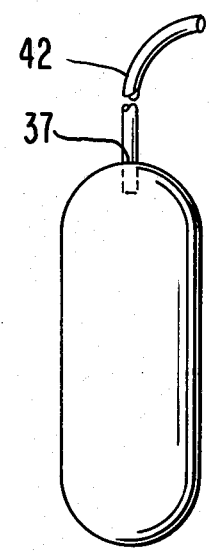
FIG. 6 is a view of an osmotic capsule with a catheter arrangement for delivering a drug to a receptor site distant from the osmotic capsule.

In an embodiment, illustrated in FIG. 6, the osmotic capsule is equipped with a conduit or tube that fits into the osmotic orifice for delivering a useful agent to a receptor distant from the osmotic capsule.

The osmotic capsules provided by the invention are made preferrably from tasteless materials that are also non-toxic to a biological recipient. The osmotic capsules are easily fitted, and they are easily self-administered by a patient. The osmotic capsule can have various shapes in addition to the oblong shaped depicted in the figures, including round, oval, tubular, and the like. The osmotic capsule can have various sizes corresponding to its internal contents. The osmotic capsule used for the purpose of the invention can be transparent, colorless, or colored to give a special product a distinctive appearance. The osmotic capsule can be filled by manual or machine filling methods. The osmotic capsule of this invention has many applications, including in a presently preferred embodiment pharmaceutical applications. The pharmaceutical applications of the osmotic capsule embrace an oral dosage form for ethical or proprietary products for human or veterinary use; as an implantable osmotic capsule for in vivo application in human and veterinary use; and the like. The osmotic capsule can be used also for packaging and delivering breath fresheners, perfumes, bath oils containing dermal medicaments, bubble baths containing therapeutics, and the like. The osmotic capsule also can be sized, shaped, structured and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, chemical reactions, and other environments of use.

DETAILED DESCRIPTION OF THE INVENTION

In accordance with the practice of this invention, it has now been found that osmotic capsules can be provided with a wall comprising a semipermeable lamina and a hydrophilic lamina which laminae mutually act as a unit integral wall in cooperative relationship with the compartment of the osmotic capsule. The semipermeable lamina is formed of a material that does not adversely affect an animal or a host, and the selectively semipermeable materials used for forming the semipermeable lamina are non-erodible and they are insoluble in fluids.

Representative materials for forming the semipermeable lamina include semipermeable homopolymers, semipermeable polymers, and the like. In one embodiment typical materials include cellulose esters, cellulose ethers, and cellulose ester-ethers. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkylsulfamate, and semipermeable polymer forming groups.

The semipermeable materials typically include a member selected from the group consisting of cellulose acylate, cellulose diacylate, cellulose triacetate, cellulose acetate, cellulose diacetate, cellulose triacetate, mono-, di- and tri-cellulose alkanylates, mono-, di- and tri-alkenylates, mono-, di- and tri-aroylates, and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8%; and the like. More specific cellulosic polymers include cellulose propionate having a D.S. of 1.8 and a propionyl content of 38.5%; cellulose acetate propionate having an acetyl content of 1.5 to 7% and an acetyl content of 39 to 42%; cellulose acetate propionate having an acetyl cntent of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acette butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate and the like; mixed cellulose esters such as cellulose acetate valerate, celluloser acetate succinate, cellulose propionate succinate, cellulose acetate octanoate, cellulose valerate palmitate, cellulose acetate heptonate, and the like. Semipermeable polymers are known in U.S. Pat. No. 4,077,407, and they can be made by procedures described in *Encyclopedia of Polymer Science and Technology*, Vol. 3, pages 325 to 354, 1964, published by Interscience Publishers, Inc., New York.

Additional semipermeable polymers include acetaldehyde dimethyl acetate; cellulose acetate ethylcarbamate; cellulose acetate methylcarbamate; cellulose dimethylaminoacetate; semipermeable polyamides; semipermeable polyurethanes; semipermeable sulfonated polystyrenes; cross-linked, selectively semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; semipermeable polystyrene derivatives; semipermeable poly(sodium styrenesulfonate); semipermeable poly(vinylbenzyltrimethyl)ammonium chloride; semipermeable polymers exhibiting a fluid permeability of 10 to 10 (cc.mil/cm.hr.atm) expressed as per atmosphere of hydrostatic or osmotic pressure difference across a semipermeable wall. The polymers are known to the art in U.S. Pat. Nos. 3,845,770; 3,916,899; and 4,160,020, and in *Handbook of Common Polymers*, by Scott, J. R. and Roff, W. J., 1971, published by CRC Press, Cleveland, Ohio.

Exemplary pH sensitive materials that keep their integrity at a pH up to 3.5 inclusive and lose their integrity at a pH greater than 3.5 are those materials that lose their integrity by dissolving, disintegrating, hydrolyzing, solubilizing or undergoing dissolution in the pH environment greater than 3.5. The presently preferred materials are enteric materials. Representative materials are polymers that keep their integrity at a pH of 1.0 to 3.5 inclusive, but undergo change in integrity at a pH greater than 3.0 are certain cellulose carboxylic acid esters, and certain carboxylic acid ethers, such as cellulose ethyl phthalate, cellulose acetate phthalate, starch acetate phthalate, amylose acetate phthalate, hydroxypropyl methylcellulose phthalate, hydroxybutyl methylcellulose phthalate, and other materials such as cellulose acetate hexahydrophthalate, hydroxypropyl methylcellulose hexahydrophthalate, and the like.

Representative of other polymers and polymer compositions comprising at least two ingredients operable for the present purpose of keeping their integrity in the pH range of 1.0 to 3.5 inclusive, but undergoes change in the pH range of 3.5 to 8.0 are polymers such as shellac, ammoniated shellac, formalized gelatin, polyvinyl acetate phthalate, polyvinyl acetate hydrogenphthalate, and the like; and polymer compositions such as a mixture of hydroxypropyl methylcellulose phthalate and ammoniated shellac in a weight or weight ratio of 99 to 1, shellac-formalized gelatin composition, styrene-maleic acid copolymer dibutyl phthalate composition, styrene-maleic acid polyvinyl acetate phthalate composition, shellac-stearic acid composition, and the like. When the lamina comprises a semipermeable polymer and a pH sensitive material, the two lamina forming ingredients are in a ratio of 65 to 95% semipermeable material and 5 to 35% pH sensitive material, on a weight basis.

The polymeric materials used for forming the hydrophilic lamina include polymers which interact with water or a biological fluid and swill or expand to an equilibrium state. The polymer thus exhibits the ability to retain a significant fraction of imbibed fluid in the polymer molecular structure. The polymers swell or expand to a very high degree, usually exhibiting a 2 to 50 fold volume increase. The swellable, hydrophilic polymers can be noncross-linked or lightly cross-linked. The cross-links can be covalent or ionic bonds with the polymer possessing the ability to swell in the presence of fluid, and when cross-linked will not dissolve in the fluid. The polymers can be of plant, animal, mineral or synthetic origin. Polymeric material useful for the present purpose include poly(hydroxyalkyl methacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinyl alcohol) having a low acetate residual; a mixture of agar and carboxymethyl cellulose; a swellable composition comprising methyl cellulose mixed with a sparingly cross-linked agar; a water-swellable copolymer produced by a dispersion of finely divided copolymer of maleic anhydride with styrene, ethylene, propylene, or isobutylene, water swellable polymer of N-vinyl lactams; polyethylene oxide; and the like.

Other polymers useful for forming a hydrophilic lamina include pectin having a molecular weight ranging from 30,000 to 300,000; gelatine; gelatin having a viscosity of 15 to 30 millipoises and bloom strength up to 150 grams; gelatin having a bloom value of 160 to 250; polysaccharides such as agar, acacia, karaya, tragacanth, algins and guar; Carbopol ® acidic carboxy polymerand its salt forms; Cyanamer ® polyacrylamides cross-linked water-swellable indene-maleic anhydride polymers; Good-rite ® polyacrylic acid having a molecular weight of 80,000 to 200,000; Polyox ® polyethylene oxide polymers having a molecular weight of 100,000 to 5,000,000; starch graft copolymers; Aqua-Keep ® acrylate polymer with water absorbability of about 400 times its weight; diester cross-linked polyglucan; a mixture of noncross-linked polyvinyl alcohol and poly(N-vinyl-2-pyrrolidone); zein available as prolamine; and the like. Representative polymers possessing hydrophilic properties are known in U.S. Pat. Nos. 3,865,108; 4,002,173; 4,207,893; and 4,327,725; and in *Handbook of Common Polymers*, by Scott and Roff, published by Cleveland Rubber Company, Cleveland, Ohio.

A plasticizer is compounded optionally with the polymer possessing hydrophilic properties for increasing its flow properties and for enhancing the workability of the polymer during manufacture of a lamina. For example, glycerin can be used for plasticizing gelatin, pectin, casein, and polyvinyl alcohol. Plasticizers such as triethyl citrate, diethyl phthalate, diethyl sebacate and the like can be used for plasticizing polyvinyl pyrrolidone, polyacrylic acid and the like. The amount of plasticizer used is from 0.05 to 30% of the weight of the composition.

Microporous materials suitable for the present purpose generally comprise preformed microporous polymeric materials, and polymeric materials that can form a microporous structure in the environment of use. The preformed materials are essentially inert, they maintain their physical and chemical integrity during the period of agent release. They can be generically described as having a sponge-like appearance that provides a supporting structure for the delivery system, and also provide a supporting structure for microscopic-sized interconnected pores or voids. The materials can be isotropic wherein the structure is homogenous throughout a cross-sectional area, or they can be anisotropic wherein the structure is nonhomogenous throughout a cross-sectional area. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, a microporous polymers are defined by the pore size, the number of pores, the tortuosity of the microporous path and the porosity which relates to the size and the number of pores. The pore size of a microporous polymer is easily ascertained by measuring the observed pore diameter at the surface of the material under the electron microscope. Generally, materials possessing from 5% to 95% pores and having a pore size of from 10 angstroms to 100 micrometers can be used for making a microporous lamina. The pore size and other parameters characterizing the microporous structure also can be obtained from flow measurements, where a liquid flux, J, is produced by a pressure difference ΔP, across the lamina. The liquid flux through a lamina with pores of uniform radius extended through the membrane and perpendicular to its surface with area A given by the relation 1:

$$J = \frac{Nr^4 \Delta P}{8\eta \Delta x} \quad (1)$$

wherein J is the volume transported per unit time and lamina area containing N number of pores of radius r, η is the viscosity of the liquid, and ΔP is the pressure difference across the lamina with thickness Δx. For this type of lamina, the number of pores N can be calculated from relation 2, wherein is the porosity defined as the ratio of void volume to total volume of the lamina; and A is the cross-sectional area of the lamina containing N pores:

$$N = \epsilon \times \frac{A}{\pi r^2} \quad (2)$$

The pore radius then is calculated from relation 3:

$$r = \left[ 8\eta \frac{\tau \cdot \Delta x \, \tau}{\Delta p \, \epsilon} \right]^{\frac{1}{2}} \quad (3)$$

wherein J is the volume flux through the lamina per unit area produced by the pressure difference P across the lamina, η, ε and Δx have the meaning defined above and τ is the tortuosity defined as the ratio of the diffusional path length in the lamina to the lamina thickness. Relations of the above type are discussed in *Transport Phenomena In Membranes,* by Lakshmina-tayanaiah, N., Chapter 6, 1969, published by Academic Press, Inc., New York.

As discussed in the above reference on page 336, in Table 6.13, the porosity of the lamina having pore radii r can be expressed relative to the size of the transported molecule having a radius a, and as the ratio of molecular radius to pore radius a/r decreases, the lamina becomes porous with respect to this molecule. That is, when the ratio a/r is less than 0.3, the lamina becomes substantially microporous as expressed by the osmotic reflection coefficient which decreases below 0.5. Microporous lamina with a reflection coefficient in the range of less than 1, usually from 0 to 0.5, and preferably less than 0.1 with respect to the active agent are suitable for fabricating the system. The reflection coefficient is determined by shaping the material in the form of a lamina and carrying out water flux measurements as a function of hydrostatic pressure difference and as a function of the osmotic pressure difference caused by the active agent. The osmotic pressure difference creates a hydrostatic volume flux, and the reflection coefficient is expressed by relation 4:

$$\sigma = \frac{\text{hydrostatic pressure difference} \times \text{osmotic volume flux}}{\text{osmotic pressure difference} \times \text{hydrostatic volume flux}} \quad (4)$$

Properties of microporous materials are described in *Science,* Vol. 170, pages 1302 to 1305, 1970; *Nature,* Vol. 214, page 285, 1967; *Polymer Engineering and Science,* Vol. 11, pages 284–288, 1971; U.S. Pat. Nos. 3,567,809 and 3,751,536; and in *Industrial Processing With Membranes,* by Lacey R. E., and Loeb, Sidney, pages 131 to 134, 1972, published by Wiley, Interscience, New York.

Microporous materials having a preformed structure are commercially available and they can be made by art-known methods. The microporous materials can be made by etching, nuclear tracking, by cooling a solution of flowable polymer below the freezing point whereby solvent separates and evaporates from the solution in the form of crystals dispersed in the polymer followed by curing the polymer to remove the solvent crystals, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes,* by R. E. Kesting, Chapters 4 and 5, 1971, published by McGraw Hill, Inc.; *Chemical Reviews,* Vol. 18, pages 373 to 455, 1934; *Polymer Eng. and Sci.,* Vol. 11, No. 4, pages 284 to 288, 1971; *J. Appl. Poly. Sci.,* Vol. 15, pages 811 to 829, 1971; and in U.S. Pat. Nos. 3,565,259; 3,615,024; 3,751,536; 3,801,692; 3,852,224; and 3,849,528.

Microporous materials useful for the present purpose include microporous polycarbonates comprised of linear polyesters of carbonic acid in which carbonate groups recur in the polymer chain, microporous materials prepared by the phosgenation of a dihydroxyl aromatic such as bisphenol A, microporous poly(vinylchloride), microporous polyamides such as polyhexamethylene adipamide, microporous modacrylic copolymers including those formed from poly(vinylchloride) 60% and acrylonitrile, styrene acrylic acid and its copolymers, porous polysulfones characterized by diphenylene sulfone groups in a linear chain thereof, halogenated poly(vinylidene), polychloroethers, acetal polymers, polyesters prepared by esterification of a dicarboxylic acid or anhydride with an alkylene polyol, poly(alkylenesulfides), phenolic polyesters, microporous poly(saccharides), microporous poly(saccarides) having substituted and unsubstituted anhydroglucose units and preferably exhibiting a higher permeability to the passage of water and biological fluids than semipermeable lamina, asymmetric porous polymers, cross-linked olefin polymers, hydrophobic or hydrophilic microporous homopolymers, copolymers or interpolymers having a reduced bulk density, and materials described in U.S. Pat. Nos. 3,597,752; 3,643,178; 3,654,066; 3,709,774; 3,718,532; 3,803,061; 3,852,224; 3,853,601; and 3,852,388, in British Pat. No. 1,126,849, and in *Chem. Abst.,* Vol 71 4274F, 22572F, 22573F, 1969.

Additional microporous materials include poly(urethanes), cross-linked, chain-extended poly(urethanes), microporous poly(urethanes) in U.S. Pat. No. 3,524,753, poly(imides), poly(benzimidazoles), collodion (cellulose nitrate with 11% nitrogen), regenerated proteins, semisolid cross-linked poly(vinylpyrrolidone), microporous materials prepared by diffusion of multivalent cations into polyelectrolyte sols as in U.S. Pat. No. 3,565,259, anisotropic permeable microporous materials of ionically associated polyelectrolytes, porous polymers formed by the coprecipitation of a polycation and a polyanion as described in U.S. Pat. Nos. 3,276,589; 3,541,055; 3,541,066 and 3,546,142, derivatives of poly(styrene) such as poly(sodium styrenesulfonate) and poly(vinylbenzyltrimethylammonium chloride), and the microporous materials disclosed in U.S. Pat. No. 3,615,024 and U.S. Pat. Nos. 3,646,178 and 3,852,224.

Further, the microporous forming material used for the purpose of the invention includes the embodiment wherein the microporous lamina is formed in situ, by a pore-former being removed by dissolving or leaching it to form the microporous lamina during the operation of the system. The pore-former can be a solid or a liquid. The term liquid, for this invention, embraces semisolids and viscous fluids. The pore-formers can be inorganic or organic. The pore-formers suitable for the invention include pore-formers that can be extracted without any chemical change in the polymer. The pore-forming solids have a size of about 0.1 to 200 micrometers and they include alkali metal salts such as sodium chloride, sodium bromide, potassium chloride, potassium sulfate, potassium phosphate, sodium benzoate, sodium acetate, sodium citrate, potassium nitrate and the like. The alkalini earth metal salts include calcium phosphate, calcium nitrate, and the like. The transition metal salts include ferric chloride, ferrous sulfate, zinc sulfate, cupric chloride, manganese fluoride, manganese fluorosilicate, and the like. The pore-formers include organic compounds such as polysaccharides. The polysaccharides include the sugars sucrose, glucose, fructose, mannitol, mannose, galactose, aldohexose, altrose, talose, sorbitol, lactose, monosaccharides and disaccharides. Also, organic aliphatic and aromatic oils, including diols and polyols, as exemplified by polyhydric alcohols, poly(alkylene glycols), polyglycols, alkylene glycols, poly(α-ω)-alkylenediols esters or alkylene glycols and the like; water soluble cellulosic polymers such as hydroxyloweralkyl cellulose, hydroxypropyl methylcellulose, methyl cellulose, methylethyl cellulose, hydroxyethyl cellulose and the like; water soluble polymers such as polyvinylpyrrolidone, sodium carboxymethylcellulose and the like. The pore-formers are nontoxic, and on their removal from the lamina channels are formed through the lamina. In a preferred embodiment, the pore-forming agents are selected from the group consisting of inorganic and organic salts, carbohydrates, poly-alkylene glycols, poly($\alpha$-$\omega$)-alkylenediols, esters of alkylene glycols, glycols, and water soluble cellulosic polymers, useful for forming a microporous lamina in a biological environment. Generally, for the purpose of this invention, when the polymer forming the lamina contains more than 20% by weight of a pore-former, the polymer is a precursor microporous lamina that on removing the pore-former, yields a lamina which is substantially microporous. At concentrations less than this, the lamina behaves like a semipermeable lamina or membrane.

The expression osmotic orifice as used herein comprises means and method suitable for releasing the useful, active agent formulation from the osmotic system. The expression includes passageway, aperture, hole, bore and the like through the semipermeable wall, or through the laminated wall. The orifice can be formed by mechanical drilling, laser drilling, or by eroding an erodible element such as a gelatin plug to yield the orifice in the environment of use. In an embodiment, the osmotic passageway in the osmotic capsule is formed in the environment of use in response to the hydrostatic pressure generated in the capsule. In another embodiment, the osmotic capsule can be manufactured with two or more osmotic passageways located anywhere on the osmotic capsule for delivering the useful agent with the capsule retaining osmotic properties. The osmotic orifice can be formed also by mechanical rupturing of the laminae during operation of the osmotic capsule. A detailed description of osmotic orifices and the maximum and minimum dimensions for an orifice are disclosed in U.S. Pat. Nos. 3,845,770 and 3,916,899.

The osmotically effective compounds that can be used for the purpose of this invention include inorganic and organic compounds that exhibit an osmotic pressure gradient across a semipermeable wall, or a semipermeable laminated wall, against an external fluid. The osmotically effective compounds imbibe fluid into the osmotic system thereby making available in situ fluid for imbibition by the hydrophilic polymer to enhance its expansion, and for forming a solution, or a suspension or the like containing useful agent for its delivery from the osmotic system. The osmotically effective compounds are known also as osmotically effective solutes, or osmagents. The osmotically effective compounds are used by mixing them with a useful agent, homogenously or heterogenously, and charging them into the compartment of the system. The osmotic solutes attract fluid into the system and they are delivered from the system concomitantly transporting dissolved and/or undissolved useful agent through the orifice to the exterior of the system. Osmotically effective solutes useful for the present purpose include magnesium sulfate, magnesium chloride, sodium chloride, lithium chloride, potassium sulfate, sodium sulfate, lithium sulfate, potassium acid phosphate, d-mannitol, urea, inositol, magnesium succinate, tartaric acid, carbohydrates such as raffinose, sucrose, glucose, $\alpha$-d-lactose monohydrate, and mixtures thereof. The amount of osmagent in the compartment will generally be from 0.01% to 35%, or higher, based on the total weight of all the components present in the compartment.

The expression useful agent formulation as used herein denotes a useful agent, a useful agent mixed with an osmagent, a useful agent mixed with a pharmaceutically acceptable carrier, or a useful agent mixed with a pharmaceutically acceptable carrier and an osmagent. The expression useful agent per se as used herein denotes any useful active agent or compound that can be delivered from the osmotic capsule to produce a beneficial and useful result. The useful agents include pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermentation agents, sex sterilants, fertility inhibitors, fertility promoters, air purifiers, microorganism attenuators, and other agents that benefit the environment of use.

In the specification and the accompanying claims, the term useful agent includes drug, and the term drug includes any physiologically or pharmacologically active substance that produces a local or systemic effect, in animals, including warm blooded mammals, humans and primates, avians, household, sport and farm animals, laboratory animals, pisces, reptiles and zoo animals. The term physiologically as used herein denotes the administration of a drug to produce normal levels and functions. The term pharmacologically denotes variations in response to amount of drug administered to the host. *Stedman's Medical Dictionary;* 1966, published by Williams and Wilkins, Baltimore, MD. The phrase drug formulation as used herein means the drug is in the compartment optionally mixed with an osmotic solute and/or with a pharmaceutical carrier. The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synoptic sites, neuroeffector junctional sites, endocrine system, hormone systems, immunological system, organ systems, reproductive system, skeletal system, autocoid systems, alimentary and excretory systems, inhibitory of autocoids and histamine systems, and physiological systems. The active drug that can be delivered for acting on these animal systems includes depressants, beta-blockers, hypnotics, sedatives, psychic energizers, tranquilizers, anti-convulsants, muscle relaxants, antiparkinson agents, analgesics, anti-inflammatories, local anesthetics, muscle contractants, antimicrobials, anti-malarials, hormonal agents, contraceptives, sympathomimetics, diuretics, anti-parasitics, neoplastics, hypoglycemics, ophthalmics, electrolytes, diagnostic agents, cardiovascular drugs, and the like.

The carriers mixed with the useful agent in the compartment in a presently preferred embodiment, are carriers are that are pharmacologically acceptable carriers that are easily excreted, metabolized, assimilated, or the like by a warm-blooded animal. The carrier medium used for the present purpose can be inorganic, or organic, and of naturally occurring or synthetic origin. Examples of carriers included in the term are substances such as solutions, suspensions, liquids, immiscible liquids, emulsions, sols, colloids, and oils. Representative carriers include liquid alkylene glycols such as ethylene glycol, diethylene glycol, triethylene glycol, ethylene glycol monomethyl ether, liquid polyethylene glycols having a molecular weight of 200, 300, 400 and higher; oils of plant, animal and marine origin such as corn oil, almond oil, babassu oil, eucalyptus oil, cottonseed oil, palm oil, peanut oil, tung oil, whale oil, herring oil, mineral oil, and the like; emulsions of castor oil in aqueous solutions of pigskin gelatin; emulsions of gum arabic, water and ethyl cellulose; liquid glyceryl triesters of a low molecular weight fatty acid; oils with emulsifiers such as mono- or di-glyceride of a fatty acid; a mixture of from about 70% to about 99.9% propylene glycol and from about 0.1% to 30% of glycerin; a mixture of from about 70% to about 99.9% propylene glycol and from about 0.1 to to 30% of ethanol; a mixture by volume of from about 80% to 99.9% of propylene glycol and from about 0.1% to about 20% of a mixture of from about 50% to 99.9% of ethanol or glycerin and from 0.1% to about 50% of sterile water; 5% dextrose in physiological saline; oils mixed with poly-oxyethylene sorbitan monolaurate; a mixture of peanut oil and beeswax; peanut oil containing pectin; glycerine and gelatin, with or without added water; glycerin/castile soap formulation; and the like.

Exemplary drugs that can be delivered by the osmotic capsule of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metoprolol tartrate, cimetidine hydrochloride, diphenidol, meclizine hydrochloride, prochlorperazine maleate, phenoxybenzamine, thiethylperazine maleate, anisindone, diphenadione erythrityl tetranitrate, dizoxin, isofurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, estrogenic progestational, corticosteriods, hydrocortisone, hydrocorticosterone acetate, cortisone acetate, triamcinolone, methyltesterone, 17β-estradiol, ethinyl estradiol, ethinyl estradiol 3-methyl ether, prednisolone, 17-hydroxyprogesterone acetate, 19-nor-progesterone, norgestrel, norethindone, norethiderone, progesterone, norgesterone, norethynodrel, aspirin, indomethacin, naproxen, fenoprofen, sulidac, diclofenac, indoprofen, nitroglycerin, propranolol, metoprolol, valproate, oxprenolol, timolol, atenolol, alprenolol, cimetidine, clonidine, imipramine, levodopa, chloropropmazine, reserpine, methyl-dopa, dihydroxyphenylalanine, pivaloyloxyethyl ester of α-methyldopa hydrochloride, theophylline, calcium gluconate ferrous lactate, ketoprofen, ibuprofen, cephalexin, erythromycin, haloperidol, zomepirac, vincamine, diazepam, phenoxybenzamine, β-blocking agents, calcium-channel blocking drugs such as nifedipine, diltiazen, verapamil, and the like. The beneficial drugs are known to the art in Pharmaceutical Sciences, edited by Remington 14th Ed., 1979, published by Mack Publishing Co., Easton, PA; The Drug, The Nurse, The Patient, Including Current Drug Handbook, 1974–1976, by Falconer, et al., published by Saunder Company, Philadelphia, PA, and Medical Chemistry, 3rd Ed., Vol. 1 and 2, by Burger, published by Wiley-Interscience, New York.

The drug can be in various forms, such as uncharged molecules, molecular complexes, pharmacologically acceptable salts such as the hydrochloride, hydrobromide, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides can be used. Also, a drug that is water insoluble can be used in a form that is a water soluble derivative thereof to serve as a solute, and on its release from the device, is converted by enzymes, hydrolyzed by body pH or other metabolic processes to the original biologically active form. The agent including drug, can be present in the compartment with a binder, dispersant, wetting agent, suspending agent, lubricant and dye. The amount of beneficial agent in an osmotic capsule generally is about from 0.05 ng to 5 g or more, with individual devices containing for example, 25 ng, 1 mg, 5 mg, 125 mg, 250 mg, 500 mg, 750 mg, 1.5 g, and the like. The osmotic capsule can be administered once, twice or thrice daily. The expression at a controlled rate as used herein means agent release from the osmotic capsule is governed by the osmotic capsule in an amount per unit time. The expression prolonged period of time means the osmotic capsule delivers the useful agent, continuously from at least 15 minutes to 750 hours.

Examples of drug carrier compositions that can be contained in the osmotic capsule include acetaminophen in vegetable oil, ascorbic acid in polysorbate, ephedrine sulfate in vegetable oil, glyceryl guaicolate in peanut oil, mephensin in polyethylene glycol 400, meprobamate in polyethylene glycol 400, procaine penicillin G in vegetable oil, tetracycline amphateric in vegetable oil, vitamin A and vitamin D in fish oil, vitamin E, in rapeseed oil, theophylline in polyethylene glycol, estrogen in an emulsified carrier containing corn oil, sorbitan trioleate, polysorbate and benzyl benzoate; and the like.

The semipermeable wall can be applied to the capsule containing the useful agent by molding, forming, spraying, or dipping the capsule into a wall forming material. Another and presently preferred technique that can be used for applying the wall is the air suspension procedure. This procedure consists in suspending and tumbling the compositions in a current of air and a wall forming composition until the wall surrounds and coats the capsule. The procedure is repeated with a different lamina forming composition to form a laminated wall. The air suspension procedure is described in U.S. Pat. No. 2,799,241; *J. Am. Pharm. Assoc.*, Vol. 48, pages 451 to 459, 1979; and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remington, 14th Edition, pages 1626 to 1678, 1970, published by Mack Publishing Co., Easton, PA.

Exemplary solvents suitable for manufacturing the laminates and laminae include inert inorganic and organic solvents that do not adversely harm the materials, the capsule, and the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

DETAILED DESCRIPTION OF EXAMPLES

The following examples are merely illustrative of the present invention, and they should not be considered as limiting the scope of the invention in any way, as these examples and other equivalents thereof will become apparent to those versed in the art in the light of the present disclosure, the drawings and the accompanying claims.

EXAMPLE 1

As osmotic capsule for the controlled delivery of the drug nifedipine is made as follows: a pharmaceutically acceptable soft capsule having a wall about 0.4 mm thick surrounding an internal lumen, and formed of a composition comprising gelatin, glycerine, water, titanium dioxide and a trace of red dye, with the lumen containing a drug formulation comprising 10 mg of nifedipine, water, sodium saccharin, mint oil and polyethylene glycol 400, is coated with a semipermeable wall forming composition. The semipermeable composition comprises 92% cellulose acetate having an acetyl content of 36% and 8% polyethylene glycol 4000, wt/wt. The cellulose acetate is prepared by blending cellulose acetate having an acetyl content of 39.8% with cellulose acetate having an acetyl content of 32%, in the ratio of 51.3% to 48.7%, wt/wt.

Figure 7:
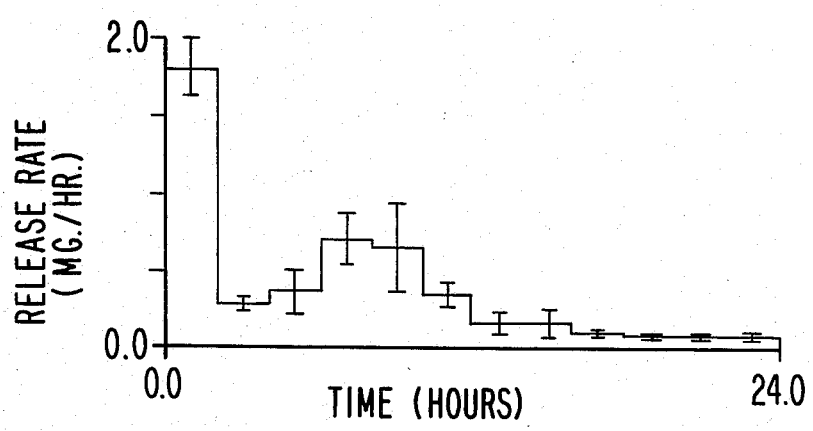
FIG. 7 is a graph depicting the release rate per unit time from an osmotic capsule; and, FIG. 8 is a graph depicting the cumulative amount released from an osmotic capsule over time.

The capsules are coated in an air suspension machine. The coating composition comprises 3% polymer solution in methylene chloride-methanol, in the ratio of 80% to 20%, wt/wt. The semipermeable wall laminated around the capsule in contacting relation weighed about 21 mg and has a thickness of about 0.05 mm. The capsule, after removal from the air suspension coater is dried in a forced air oven at 40 C. for 48 hours. Then, an orifice having a diameter of 0.99 mm is laser drilled through the semipermeable laminated capsule wall for delivering the drug from the osmotic capsule. The release rate, in mg. per hr. for nifedipine is illustrated in FIG. 7.

EXAMPLE 2

An osmotic capsule is prepared as follows: a hard, two component capsule having a wall comprising gelatin, erythrosin, iron oxide and titanium dioxide, that surrounds and defines an internal lumen containing a drug formulation comprising 500 mg of cephradine, talc, magnesium stearate and lactose, is surrounded with a laminated semipermeable wall of cellulose acetate having an acetyl content of 32% using an air suspension coater. A 5% polymer solution in acetone-water, 90:10, wt/wt, is used for forming a semipermeable wall 0.075 mm thick. A passageway having a diameter of 0.25 mm is laser drilled through the dual, outer semipermeable-inner capsule wall for delivering the drug from the osmotic capsule in a therapeutically effective amount over time.

EXAMPLE 3

An osmotic capsule is prepared by following the procedure of Example 2 with all conditions as previously described except as recorded herein. In this example, the inner capsule comprises a hard gelatin capsule of size No. 1. The capsule contains in its lumen 300 mg of rifampicin and calcium stearate. The semipermeable wall and the passageway are as described previously.

EXAMPLE 4

An osmotic, therapeutic capsule for the controlled and continuous delivery of the beneficial drug carbocremene chlorhydrate is prepared as follows: a soft capsule having a wall comprising gelatin, glycerine, sorbitol, potassium sorbate and titanium dioxide and a thickness of about 0.5 mm, which wall surrounds and forms a closed, hollow inner space containing 150 mg of carbocremene chlorhydrate, peanut oil, soy oil, and vegetable oil, is coated with a semipermeable wall. The semipermeable wall is formed by blending 170 g of cellulose acetate having an acetyl content of 39.4% in 400 ml of methylene chloride and 400 ml of methanol which is spray coated in an air suspension machine. The coated capsule is dried for 72 hours at 35° C., and then a 0.9 mm orifice is laser drilled through the semipermeable cellulosic walls. The semipermeable wall has a thickness of about 0.27 mm.

EXAMPLE 5

The procedure of Example 5 is repeated with all conditions and procedures as previously indicated except for the changes noted in this example. In this example, the soft, elastic capsule wall consists essentially of 10 parts gelatin, 1 part acacia, 10 parts glycerin and 16 parts water, based on weight. The drug formulation in the lumen consists essentially of 250 mg of ethosuximide, polyethylene glycol 400, gelatin, glycerine, water and red dye. The semipermeable lamina, coated around the capusle in bonding relation is formed from a 5% solution consisting essentially of cellulose acetate having an acetyl content of 38.3%. The osmotic passageway is 0.25 mm in diameter.

EXAMPLE 6

Figure 8:
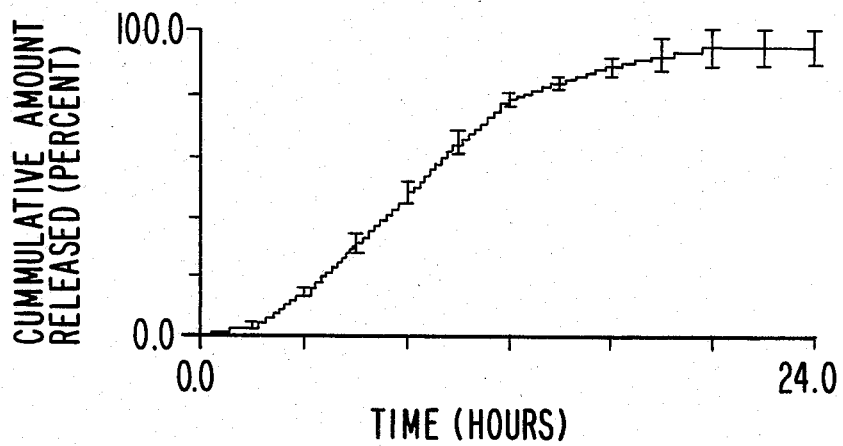

An osmotic capsule for the controlled delivery of theophylline is prepared using a soft capsule containing a drug formulation consisting essentially of 100 mg of anhydrous theophylline in propylene glycol. The capsule is coated with a semipermeable wall comprising 92% cellulose acetate having an acetyl content of 36%, and 8% polyethylene glycol 4000 wt/wt. The osmotic capsule weighs 451 mg, the semipermeable wall weighs about 11 mg and is 0.05 mm thick, the capsule containing the drug formulation weighs about 440 mg and the gelatin composition forming the capsule wall is about 0.5 mm thick, the osmotic passageway has a diameter of about 0.99 mm and the cumulative amount of drug released is illustrated in FIG. 8. In the graph, the bars represent the standard error of the means.

EXAMPLE 7

A hard capsule consisting of two sections, one slipping over the other thus completely surrounding an internal space for housing a drug formulation, is dry filled with a drug formulation consisting essentially of 500 mg of the antibacterial sodium cloxacillin, lactose, hydroxypropyl methylcellulose and lactose. The hard wall of the capsule consisting essentially of gelatin containing 0.15% sulfur dioxide to prevent decomposition during manufacturing, FD&C orange dye, and titanium dioxide opacifying agent. The capsule is coated with a semipermeable wall-forming composition of 90% cellulose acetate having an acetyl content of 38.3% and 10% polyethylene glycol having a molecular weight of 400. Finally, a passageway having a diameter of 0.25 mm is drilled through the dual cellulosic-gelatin walls to yield the osmotic, therapeutic capsule system.

EXAMPLE 8

An osmotic capsule is prepared according to the procedure of Example 1. The capsule wall consists essentially of gelatin, glycerin, sorbitol and water. The capsule contains 50,000 I.U. of vitamin A in olive oil. The semipermeable wall encapsulating the capsule consists essentially of 88% cellulose acetate having an acetyl content of 32% and 12% sorbitol. The diameter of the osmotic passageway is about 0.2 mm.

EXAMPLE 9

An osmotic capsule is prepared for delivering vitamin E, alpha-tocopherol, by following the above procedures. The soft capsule contained 600 I.U. of vitamin E, an antioxidant mixture of butylated hydroxytoluene and butylated hydroxyanisole dissolved in benzyl alcohol, the emulsifier polyoxyethylene sorbitan monoleate, and the glyceride glyceryl triester of caproic acid. The semipermeable wall intimately laminated to the capsule consists essentially of 90% cellulose acetate having an acetyl content of 32%, 6% hydroxypropylmethylcellulose, and 4% polyethylene glycol 400. The passageway diameter is about 0.3 mm. In a water bath at 37 C., the osmotic capsule delivered substantially 100% of the vitamin formulation.

An embodiment of the invention pertains to a method for administering a beneficial drug at a controlled rate to the gastrointestional tract of a warm-blooded animal, which method comprises: (A) admitting into the gastrointestional tract an osmotic capsule comprising: (1) a capsule comprising a body and a matching cap telescopically joined to define a lumen; (2) a beneficial drug formulation in the lumen in a dosage unit amount for performing a therapeutic program; (3) a lamina surrounding the capsule, the lamina formed of a semipermeable polymeric composition permeable to the passage of aqueous and biological fluid and substantially impermeable to the passage of drug formulation; and, (4) an osmotic orifice through the exterior lamina and the capsule for communicating with the exterior of the osmotic capsule and the internal lumen; (B) imbibing fluid through the semipermeable lamina and into the capsule at a rate determined by the permeability of the semipermeable lamina and the osmotic pressure gradient across the semipermeable lamina to form a fluidic composition that is hydrodynamically and osmotically pumped from the osmotic capsule; and (C) delivering the beneficial drug formulation in a therapeutically effective amount through the orifice at a controlled rate to the gastrointestinal tract to produce the desired medical effect over a prolonged period of from 15 minutes to 24 hours.

The invention embraces also a method for administering a beneficial drug formulation to the gastrointestional tract, wherein the osmotic capsule comprises an exterior semipermeable lamina, and an interior soft capsule manufactured as a single lamina comprising a nontoxic material that does not adversely affect the drug, is permeable to external aqueous and biological fluids imbibed into the capsule, and swells, then ultimately dissolves or bioerodes in the presence thereof to innocuous products.

Inasmuch as the foregoing specification comprises preferred embodiments of the invention, it is understood that variations and modifications may be made herein in accordance with the inventive principles disclosed, without departing from the scope of the invention.

We claim:

1. An osmotic capsule for the delivery at a controlled rate of a beneficial agent formulation to a fluid environment of use, the osmotic capsule comprising:
   (a) a lamina comprising in at least a part of a semipermeable composition that substantially maintains its integrity in the environment of use, is permeable to the passage of fluid present in the environment of use, and substantially impermeable to the passage of a beneficial agent formulation, the lamina surrounding:
   (b) a capsule comprising a hydrophilic body and a matching cap telescopically joined to define a lumen;
   (c) a beneficial agent formulation in the lumen, said formulation a member selected from the group consisting of solid, powdered, pulverized, micronized and particle formulations that form, when the osmotic capsule is in operation in the environment of use in the presence of fluid that enters the osmotic capsule, a member selected from the group consisting of a solution and suspension; and,
   (d) at least one orifice through the lamina and the capsule communicating with the lumen and the exterior of the osmotic capsule for delivering the beneficial agent formulation from the osmotic capsule.

2. The osmotic capsule for the delivery at a controlled rate of the beneficial agent formulation according to claim 1, wherein the semipermeable composition is a member selected from the group consisting of cellulose acylate, cellulose diacylate, cellulose triacylate, cellulose acetate, cellulose diacetate, cellulose triacetate, cellulose ester, and cellulose acetate butyrate.

3. The osmotic capsule for the delivery at a controlled rate the beneficial agent formulation according to claim 1, wherein a lamina comprising a microporous composition is in laminar arrangement with the lamina formed of the semipermeable material.

4. The osmotic capsule for the delivery at a controlled rate the beneficial agent according to claim 1, wherein the capsule comprises a member selected from the group consisting of poly(hydroxyalkyl methacrylate), gelatin, polyethylene oxide, polyvinyl pyrrolidone and polyvinyl alcohol.

5. The osmotic capsule for the delivery at a controlled rate the beneficial agent formulation according to claim 1, wherein the capsule comprises a composition comprising a plasticizer and a hydrophilic polymer that expands and retains fluid imbibed into the osmotic capsule.

6. The osmotic capsule for the delivery at a controlled rate the beneficial agent formulation according to claim 1, wherein the capsule comprises a composition that exhibits an osmotic pressure gradient across the semipermeable material against an external fluid and erodes in the presence of fluid imbibed into the lumen.

7. The osmotic capsule for delivering at a controlled rate the beneficial agent according to claim 1, wherein the agent is a drug and the lumen contains a nontoxic carrier.

8. An osmotic capsule for the delivery at a controlled rate of a beneficial agent formulation to a fluid environment of use, the osmotic capsule comprising:
（a) a lamina comprising in at least a part a semipermeable composition that substantially maintains its integrity in the environment of use, is permeable to the passage of fluid present in the environment of use and is substantially impermeable to the passage of beneficial agent formulation, the lamina surrounding:
(b) a one piece capsule comprising a hydrophilic lamina capsuling a lumen;
(c) a beneficial agent formulation in the lumen, said formulation a member selected from the group consisting of solid, powdered pulverized, micronized and particle formulations that form, when the osmotic capsule is in operation in the environment of use in the presence of fluid that enters the osmotic capsule, a member elected from the group consisting of a solution and suspension; and,
(d) at least one orifice through the lamina and the capsule communicating with the lumen and the exterior of the osmotic capsule for delivering the beneficial agent formulation from the osmotic capsule.

9. The osmotic capsule for the delivery at a controlled rate the beneficial agent formulation according to claim 8, wherein the semipermeable composition is a member selected from the group consisting of cellulose acylate, cellulose diacylate, cellulose triacylate, cellulose acetate, cellulose diacetate, and cellulose triacetate, cellulose ester, and cellulose acetate butyrate.

10. The osmotic capsule for the delivery at a controlled rate the beneficial agent formulation according to claim 8, wherein a lamina comprising a microporous composition is in laminar arrangement with the lamina formed of a semipermeable material.

11. The osmotic capsule for the delivery at a controlled rate the beneficial agent formulation according to claim 8, wherein the lamina comprising the capsule is a hydrophilic material selected from the group consisting of poly(hydroxyalkyl methacrylate), gelatin, polyethylene oxide, polyvinyl pyrrolidone, and polyvinyl alcohol.

12. The osmotic capsule for the delivery at a controlled rate the beneficial agent formulation according to claim 8, wherein the lamina comprising the capsule comprises a composition of a hydrophilic polymer and a plasticizer.

13. The osmotic capsule for the delivery at a controlled rate the beneficial agent formulation according to claim 8, wherein the lamina comprising the capsule exhibits an osmotic pressure gradient across the semipermeable material against an external fluid and swells, then erodes in the presence of fluid imbibed into the osmotic capsule.

14. The osmotic capsule for the delivery at a controlled rate the beneficial agent formulation according to claim 8, wherein the agent is a drug, and the capsule contains a nontoxic carrier.

15. An osmotic capsule comprising a member selected from the group consisting of a single section and a two section capsule for the controlled delivery of a beneficial drug formulation to a biological environment of use, the osmotic capsule comprising:
(a) a shaped wall comprising an inner lamina comprising a composition permeable to the passage of fluid present in the environment of use, and an outer lamina comprising a composition permeable to the passage of fluid present in the environment of use and substantially impermeable to the passage of drug formulation, the wall capsuling:
(b) a compartment;
(c) a dosage unit amount of a drug formulation in the compartment, said formulation a member selected from the group consisting of solid, powdered, pulverized, micronized and particle formulations that form, when the osmotic capsule is in operation in the environment of use and in the presence of fluid that enters the osmotic capsule, a member selected from the group consisting of a solution and suspension; and,
(d) at lease one orifice in the shaped wall communicating with the compartment and the exterior of the osmotic capsule for delivering the drug formulation to the environment of use over a prolonged period of time.

16. The osmotic capsule for the controlled delivery of the beneficial drug formulation according to claim 15, wherein the drug formulation exhibits an osmotic pressure gradient across the shaped wall against a fluid present in the environment of use.

17. The osmotic capsule for the controlled delivery of the beneficial drug formulation according to claim 15, wherein the drug formulation comprises an osmotically effective compound that exhibits an osmotic pressure gradient across the shaped wall against a fluid present in the environment of use.

18. The osmotic capsule for the controlled delivery of the beneficial drug formulation according to claim 15, wherein the compartment contains a pharmaceutically acceptable carrier.

19. The osmotic capsule for the controlled delivery of the beneficial drug formulation according to claim 15, wherein a lamina comprising a microporous composition is in laminar arrangement with the outer lamina.

20. The osmotic capsule for the controlled delivery of the beneficial drug formulation according to claim 15, wherein the osmotic capsule is a hard osmotic capsule.

21. The osmotic capsule for the controlled delivery of the beneficial drug formulation according to claim 15, wherein the osmotic capsule is a soft osmotic capsule.

22. The osmotic capsule for the controlled delivery of the beneficial drug formulation according to claim 15, wherein the environment of use is the gastrointestinal tract.

23. The osmotic capsule for the controlled delivery of the beneficial drug formulation according to claim 15, wherein the environment of use is a human and the osmotic capsule is shaped and sized for oral admittance into the human.

24. The osmotic capsule for the controlled delivery of the beneficial drug formulation according to claim 15, wherein the inner lamina is soluble in aqueous and biological fluids.

25. The osmotic capsule for the controlled delivery of the beneficial drug formulation according to claim 15, wherein the inner lamina is cross-linked.

26. The osmotic capsule for the delivery at a controlled rate of the beneficial drug formulation according to claim 15, wherein the orifice is formed when the osmotic capsule is in the environment of use.

* * * * *